US009677936B2

(12) United States Patent
Han et al.

(10) Patent No.: US 9,677,936 B2
(45) Date of Patent: Jun. 13, 2017

(54) SPECTRO-SENSOR AND SPECTROMETER EMPLOYING THE SAME

(71) Applicant: SAMSUNG ELECTRONICS CO., LTD., Suwon-si (KR)

(72) Inventors: Seunghoon Han, Seoul (KR); Hongkyu Park, Yongin-si (KR); Moonsook Lee, Seoul (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 90 days.

(21) Appl. No.: 14/707,537

(22) Filed: May 8, 2015

(65) Prior Publication Data

US 2015/0323385 A1 Nov. 12, 2015

(30) Foreign Application Priority Data

May 9, 2014 (KR) .................. 10-2014-0055755
Aug. 5, 2014 (KR) .................. 10-2014-0100697

(51) Int. Cl.
| | |
|---|---|
| *G01J 3/00* | (2006.01) |
| *G01J 3/28* | (2006.01) |
| *G01J 3/44* | (2006.01) |
| *B82Y 15/00* | (2011.01) |
| *G01N 21/552* | (2014.01) |
| *G01N 21/64* | (2006.01) |
| *G01N 21/65* | (2006.01) |
| *G01J 3/36* | (2006.01) |

(Continued)

(52) U.S. Cl.
CPC .............. *G01J 3/28* (2013.01); *B82Y 15/00* (2013.01); *G01J 3/36* (2013.01); *G01J 3/44* (2013.01); *G01J 3/4412* (2013.01); *G01N 21/554* (2013.01); *G01N 21/648* (2013.01); *G01N 21/658* (2013.01); *B82Y 20/00* (2013.01); *B82Y 30/00* (2013.01); *G01N 2021/258* (2013.01); *Y10S 977/953* (2013.01)

(58) Field of Classification Search
CPC ..... B82Y 15/00; G01J 3/02; G01J 3/44; G01J 3/28; G01N 21/31; G01N 21/55
See application file for complete search history.

(56) References Cited

U.S. PATENT DOCUMENTS 5,615,673 A 4/1997 Berger et al.
8,355,767 B2 1/2013 Bunter et al.
(Continued)

FOREIGN PATENT DOCUMENTS

KR 1020120077417 A 7/2012
KR 101271696 B1 6/2013

OTHER PUBLICATIONS

Communication issued Oct. 2, 2015, issued by the European Patent Office in counterpart European Patent Application No. 15166742.5.
(Continued)

*Primary Examiner* — Abdullahi Nur
(74) *Attorney, Agent, or Firm* — Sughrue Mion, PLLC

(57) ABSTRACT

Provided is a spectro-sensor which includes a nano antenna array. The nano antenna array includes a plurality of nano antennas which have different resonance wavelength bands and an optical detector array which includes a plurality of optical detectors that respectively detect light from the plurality of nano antennas.

23 Claims, 12 Drawing Sheets

(51) Int. Cl.
*B82Y 20/00* (2011.01)
*B82Y 30/00* (2011.01)
*G01N 21/25* (2006.01)

(56) References Cited

U.S. PATENT DOCUMENTS

| | | |
|---|---|---|
| 8,462,334 B2 | 6/2013 | Lu et al. |
| 8,480,958 B2 | 7/2013 | Gomez Rivas et al. |
| 2012/0035442 A1 | 2/2012 | Barman et al. |
| 2012/0129269 A1* | 5/2012 | Choi .................. A61B 5/0075 |
| | | 436/164 |
| 2012/0170097 A1 | 7/2012 | Han et al. |
| 2013/0148194 A1 | 6/2013 | Altug et al. |

OTHER PUBLICATIONS

S. Zhang et al., "Anti-Hermitian Plasmon Coupling of an Array of Gold Thin-Film Antennas for Controlling Light at the Nanoscale", Physical Review Letter, 2012 American Physical Society, Nov. 9, 2012.

\* cited by examiner

SPECTRO-SENSOR AND SPECTROMETER EMPLOYING THE SAME

CROSS-REFERENCE TO RELATED APPLICATIONS

This application claims priority from Korean Patent Application No. 10-2014-0055755, filed on May 9, 2014, and from Korean Patent Application No. 10-2014-0100697, filed on Aug. 5, 2014, in the Korean Intellectual Property Office, the disclosures of which are incorporated herein by reference in their respective entireties.

BACKGROUND

1. Field

Exemplary embodiments relate to a spectro-sensor which uses a nano antenna array and a spectrometer which employs the spectro-sensor.

2. Description of the Related Art

Raman spectroscopy is used to measure inelastic scattering occurring in an object due to excitation light irradiated onto the object in order to conduct component analysis of various materials.

However, it is very difficult to measure inelastic scattering because of a low signal strength thereof. To cope with this disadvantage, a configuration for amplifying the signal strength is needed, and thus, the structure of an optical system configured to measure inelastic scattering becomes quite bulky.

Recently, various studies have been carried out to develop data analysis methods and downsized Raman sensors for reducing a spectrometer structure and improving the performance thereof.

SUMMARY

Provided are a spectro-sensor which uses a nano antenna array and a spectrometer which employs the spectro-sensor.

Additional aspects will be set forth in part in the description which follows and, in part, will be apparent from the description, or may be learned by practice of the presented exemplary embodiments.

According to an aspect of one or more exemplary embodiments, a spectro-sensor includes a nano antenna array which includes a first nano antenna and at least a second nano antenna that have different respective resonance wavelength bands and an optical detector array which includes a first optical detector and at least a second optical detector that respectively detect light from the first nano antenna and the at least the second nano antenna.

Each of the first nano antenna and the at least the second nano antenna may include a respective support and a respective plurality of plasmonic nanoparticles arranged on the corresponding support.

For each of the first nano antenna and the at least the second nano antenna, the respective plasmonic nanoparticles may be formed in a form in which a conductive material is embossed.

For each of the first nano antenna and the at least the second nano antenna, the respective plasmonic nanoparticles may be formed in a form in which a conductive material is engraved.

For each of the first nano antenna and the at least the second nano antenna, the respective support may be formed of a dielectric material.

For each of the first nano antenna and the at least the second nano antenna, the respective support may be formed of a material that has at least one optical characteristic that varies based on an external signal.

The external signal may include at least one from among an electric signal, a sound wave, heat, and a mechanical force.

Each of the first nano antenna and the at least the second nano antenna may include a respective upper nano-structure layer that has a first stacked structure in which a first dielectric layer that has a first refractive index and a second dielectric layer that has a second refractive index that is higher than the first refractive index are stacked alternately along a first direction, and a respective first plurality of nano holes formed to pass through the first stacked structure, a respective lower nano-structure layer that has a second stacked structure in which a third dielectric layer that has a third refractive index and a fourth dielectric layer that has a fourth refractive index that is higher than the third refractive index are stacked alternately along the first direction, and a respective second plurality of nano holes formed to pass through the second stacked structure, and a respective intermediate layer of dielectric material disposed between the corresponding upper nano-structure layer and the corresponding lower nano-structure layer.

A period of the first nano antenna and the at least the second nano antenna that corresponds to each of the first stacked structure and the second stacked structure may be smaller than $\lambda/2$, wherein $\lambda$ represents a resonance wavelength of the first nano antenna and the at least the second nano antenna.

Each of the first plurality of nano holes and the second plurality of nano holes may be arranged according to a predetermined rule on a plane perpendicular to the first direction.

A period that corresponds to the predetermined rule may be smaller than $\lambda/3$, wherein $\lambda$ represents a resonance wavelength of the first nano antenna and the at least the second nano antenna.

The first dielectric layer and the third dielectric layer may be formed of a first same material, and the second dielectric layer and the fourth dielectric layer may be formed of a second same material.

Each of the plurality of nano holes may be filled with at least one from among air and a dielectric material which has a refractive index greater than one.

Each of the plurality of nano holes formed in the upper nano-structure layer is connected to a corresponding one of the plurality of nano holes formed in the lower nano-structure layer by passing through the intermediate layer.

According to another aspect of one or more exemplary embodiments, a spectro-sensor module includes a light source configured to irradiate excitation light toward an object and a spectro-sensor including a nano antenna array which includes a plurality of nano antennas that have different resonance wavelength bands and an optical detector array that includes a plurality of optical detectors that respectively detect light from the plurality of nano antennas, the spectro-sensor being configured to sense scattered light incident thereon that originates from the irradiated excitation light.

The spectro-sensor may be configured to sense the scattered light reflected from the object.

The spectro-sensor module may further include a base that is formed of a transmissive material and includes a first surface and a second surface that faces the first surface, in which the light source is arranged on the first surface and configured to irradiate the excitation light toward the object through the second surface, and the spectro-sensor is arranged on the first surface and configured to sense the scattered light incident from the object through the second surface.

The spectro-sensor module may further include an optical lens that is arranged on the second surface and configured to collect the excitation light irradiated from the light source toward the object and to collect the scattered light scattered from the object.

The transmissive material may be flexible.

The spectro-sensor module may be configured to be worn on the object.

The spectro-sensor may be configured to sense the scattered light which passes through the object.

The spectro-sensor module may be configured to be worn on the object in a form of an earring.

According to another aspect of one or more exemplary embodiments, a spectrometer includes a spectro-sensor module which includes a light source configured to irradiate excitation light toward an object and a spectro-sensor which includes a nano antenna array that includes a plurality of nano antennas having different resonance wavelength bands and an optical detector array that includes a plurality of optical detectors that respectively detect light from the plurality of nano antennas, the spectro-sensor being configured to sense scattered light incident thereon that originates from the irradiated excitation light, and a signal processor configured to analyze at least one physical property of the object based on a signal output by the spectro-sensor.

The light source may be further configured to irradiate light in a near infrared band.

The signal processor may be further configured to analyze the at least one physical property of the object by using Raman spectroscopy.

The spectro-sensor module may be configured to be worn on the object.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
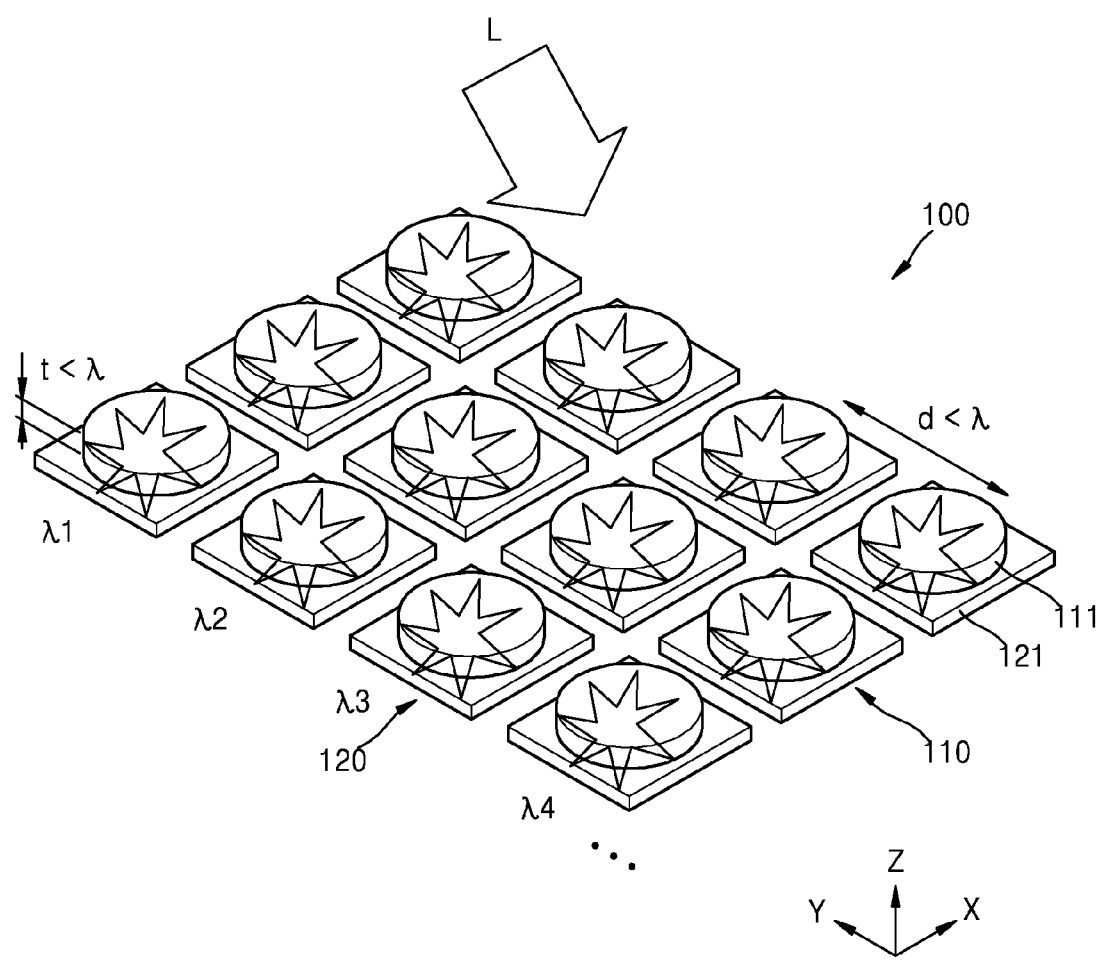
FIG. 1 is a conceptual diagram for describing schematic structure and operations of a spectro-sensor, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

Hereinafter, the exemplary embodiments will be described in detail with reference to the accompanying drawings. Throughout the drawings, like reference numerals refer to like components, and the size of each component may have been exaggerated for clarity and convenience of description in the drawings. Embodiments described below are merely exemplary and various modifications may be possible from the exemplary embodiments. In the following description, an expression such as "above" or "on" may include "on in a non-contact manner" as well as "directly on in a contact manner".

FIG. 1 is a conceptual diagram for describing schematic structure and operations of a spectro-sensor 100, according to an exemplary embodiment.

The spectro-sensor 100 may include a nano antenna array 110 which includes a plurality of nano antennas 111 having different respective resonance wavelength bands and an optical detector array 120 which includes a plurality of optical detectors 121 configured for detecting light from the plurality of nano antennas 111.

Each nano antenna 111 delivers a specific wavelength of an optical signal L from a spectroscopic-analysis target to the optical detector 121. To this end, in order to resonate and deliver specific wavelength components of lights incident at various angles, a material and a structure are determined for the respective nano antennas 111. The manner of delivery of the wavelength components may be actual traveling of light or near-field-based energy delivery. If resonance wavelengths are different between adjacent nano antennas 111, an energy distribution of light (in the form of a spatial mode) which resonates in the nano antenna 111 may intersect between the adjacent nano antennas 111.

A thickness of each of the nano antennas 111 and an interval between the nano antennas 111 have dimensions which are on the order of a sub-wavelength, and the nano antennas 111 function to intensively collect light in a predetermined wavelength band. It is known that this function is based on surface plasmon resonance which occurs at an interface between a metallic material and a dielectric material, and a resonance wavelength varies according to a detailed pattern of the nano antennas 111.

In the current exemplary embodiment, the nano antennas 111 forming the nano antenna array 110 may be configured to have different resonance wavelengths on an antenna-by-antenna basis or on a group-by-group basis, in which the nano antennas 111 may be grouped. Alternatively, the nano antennas 111 may be arranged to have different resonance wavelengths on a row-by-row basis or on a column-by-column basis.

The optical detector 121 may include any of various types of sensors which are configured for converting incident light thereon into an electric signal, such as, for example, a photo diode, a Charge Coupled Device (CCD), a Complementary Metal-Oxide Semiconductor (CMOS), Image Sensor, and/or the like.

The nano antenna array 110 and the optical detector array 120 are arranged to optically deliver a signal from the nano antenna array 110 to the optical detector array 120. For example, to reduce an optical loss, the nano antenna array 110 and the optical detector array 120 may have an integrated form. The optical detector array 120 may be directly formed on the nano antenna array 110 to physically contact with each other, however, the exemplary embodiments are not limited to such a structure.

Once light L which includes various wavelength components is incident to the spectro-sensor 100, the light L is reflected and scattered in various directions by nano patterns forming the surface of the nano antenna array 110. At this time, light in resonance wavelength bands of the nano antennas 111 are resonated and amplified in nano regions of the nano antennas 111 without being reflected or scattered in different directions. Thus, light of various wavelength components included in the incident light L is collected from within a proximity to the nano antennas 111, and the collected light is detected by the optical detector 121 which corresponds to each nano antenna 111, thus producing a high signal-to-noise ratio (SNR). The resonance wavelength bandwidths of the nano antennas 111 may be formed to be relatively narrow, such that the spectro-sensor 100 according to the current exemplary embodiment may have a high resolution.

The spectro-sensor 100 according to the current exemplary embodiment is structured such that the optical detector array 120 and the nano antenna array 110 are integrated, thereby reducing a loss caused by an optical path and increasing an SNR. Moreover, the nano antenna array 110 may also be formed in a semiconductor manufacturing process in which the optical detector array 120 is formed, thereby simplifying the overall process.

Figure 2A:
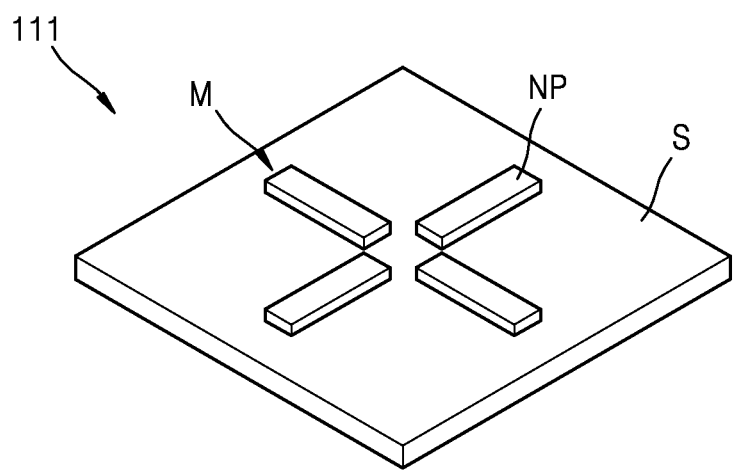
FIGS. 2A and 2B illustrate exemplary structures of a nano antenna employed in a spectro-sensor illustrated in FIG. 1.
Figure 2B:
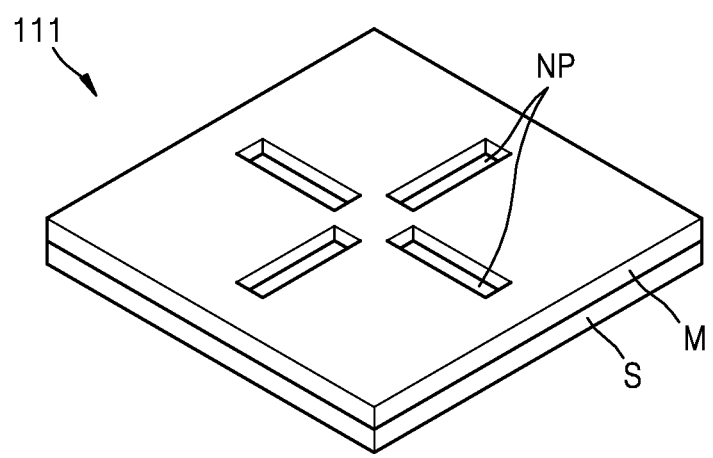

FIGS. 2A and 2B illustrate exemplary structures of the nano antenna 111 employed in the spectro-sensor 100 illustrated in FIG. 1.

Referring to FIGS. 2A and 2B, the nano antenna 111 includes a support S and a plurality of plasmonic nanoparticles NP disposed on the support S.

The plasmonic nanoparticle NP may have a form in which a conductive material M is embossed, as illustrated in FIG. 2A, or is engraved, as illustrated in FIG. 2B.

The conductive material M may include a high-conductivity metallic material that is conducive to surface plasmon excitation. For example, the conductive material M may include at least one selected from a group consisting of copper (Cu), aluminum (Al), nickel (Ni), iron (Fe), cobalt (Co), zinc (Zn), titanium (Ti), ruthenium (Ru), rhodium (Rh), palladium (Pd), white gold (i.e., platinum) (Pt), silver (Ag), osmium (Os), iridium (Ir), and gold Au, and/or an alloy which includes any one selected from the group. A two-dimensional material having high conductivity such as graphene, or a conductive oxide may be used.

The support S may include a dielectric material and/or a flexible material. The support S is not limited to the illustrated shape, and the supports S provided in the respective nano antennas 111 may be connected to form one dielectric board.

The support S may also include a material which has optical characteristics that vary with an external signal, such as, for example, an electric signal, elastic waves, heat, a mechanical force, and/or the like. For instance, an electro-optic material which has an effective refractive index that changes upon application of an electric signal, for example, a conductive oxide such as indium tin oxide (ITO) or indium zinc oxide (IZO), $LiNbO_3$, $LiTaO_3$, and/or the like may be employed for the support S. A material which has a refractive index that changes due to a phase transition at a predetermined temperature upon application of heat may be used for the support S. The material may include, for example, any of $VO_2$, $VO_2O_3$, EuO, MnO, CoO, $CoO_2$, $LiCoO_2$, $Ca_2RuO_4$, and/or the like.

When the support S includes a material which has optical characteristics that change in response to an external signal, the spectro-sensor 100 properly adjusts a signal to be applied to the support S in order to change a resonance wavelength band of the corresponding nano antenna 111.

Although the nano antenna 111 is illustrated as including four plasmonic nanoparticles NP having the same rod shape, such illustration is an exemplary one. The plasmonic nanoparticles NP included in the nano antenna 111 may have different shapes, and the number and arrangement of plasmonic nanoparticles NP may also vary.

FIGS. 3A, 3B, 3C, 3D, and 3E illustrate exemplary arrangements of plasmonic nanoparticles employed in the nano antenna 111 illustrated in FIG. 2.

Figure 3A:
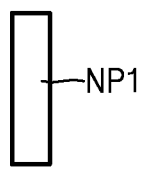
FIGS. 3A, 3B, 3C, 3D, and 3E illustrate exemplary arrangements of plasmonic nanoparticles employed in a nano antenna illustrated in FIGS. 2A and 2B.
Figure 3A:
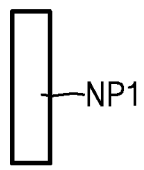
Figure 3B:
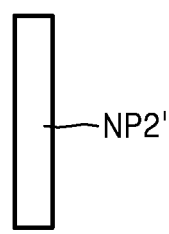
Figure 3B:
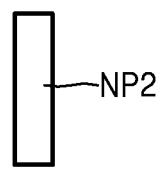
Figure 3C:
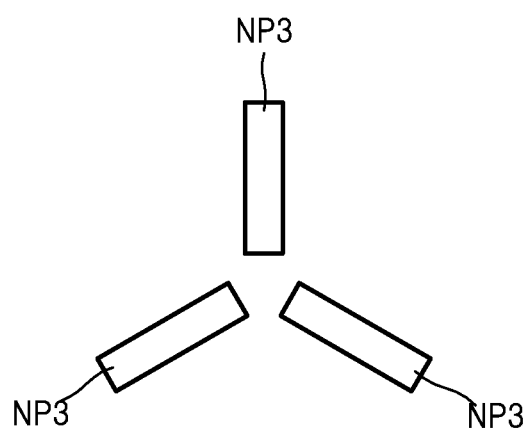
Figure 3D:
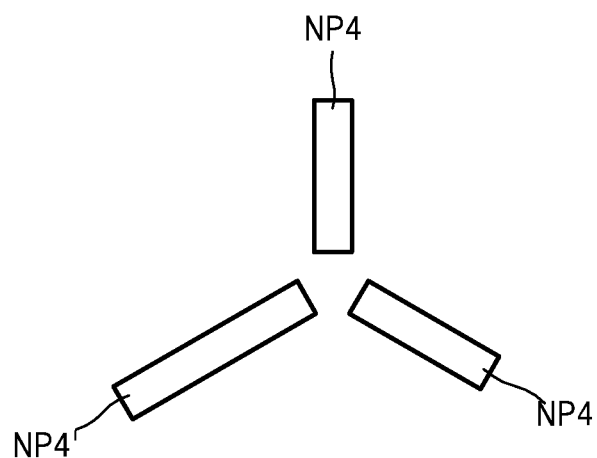
Figure 3E:
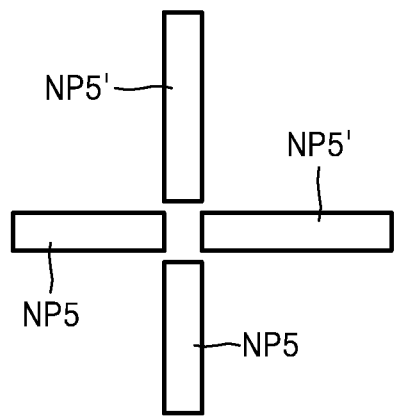

As illustrated in FIG. 3A, two plasmonic nanoparticles NP1 which have a same shape may be employed. As illustrated in FIG. 3B, two plasmonic nanoparticles NP2 and NP2' having different lengths may be employed. As illustrated in FIG. 3C, three plasmonic nanoparticles NP3 which have a same shape may be employed. As illustrated in FIG. 3D, two plasmonic nanoparticles NP4 which have the same shape and a plasmonic nanoparticle NP4' which have a different length may be employed. As illustrated in FIG. 3E, two pairs of plasmonic nanoparticles NP5 and NP5' which have two different shapes may be employed.

Although plasmonic nanoparticles in rod shapes are illustrated in FIGS. 3A, 3B, 3C, 3D, and 3E, the plasmonic nanoparticles may also have polygonal, circular, oval, wire grid shapes or other shapes. The illustrated shapes may have an embossed pattern, as illustrated in FIG. 2A, or an engraved pattern, as illustrated in FIG. 2B.

Figure 4:
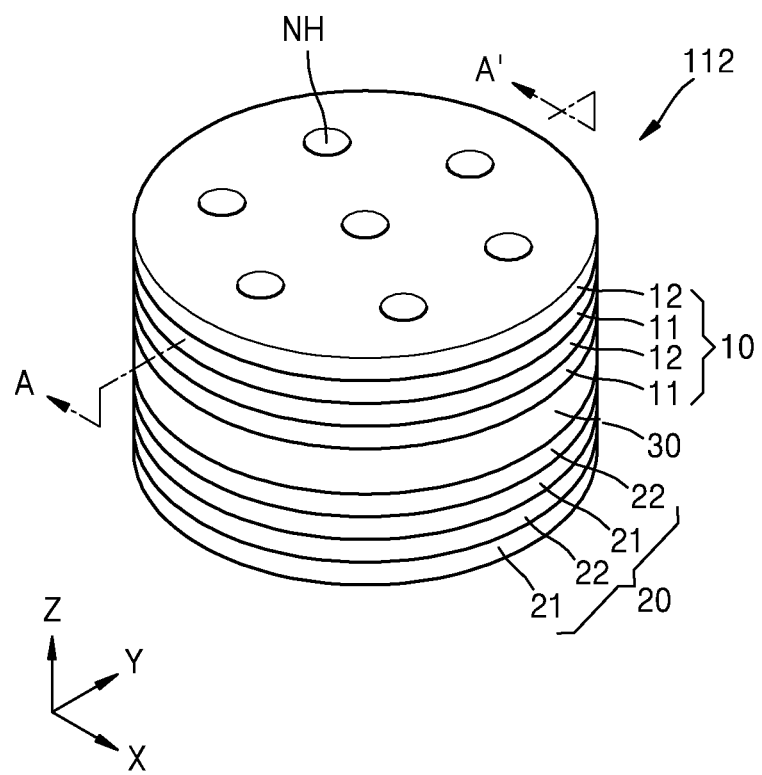
FIG. 4 illustrates another exemplary structure of a nano antenna adoptable in a spectro-sensor illustrated in FIG. 1.
Figure 5:
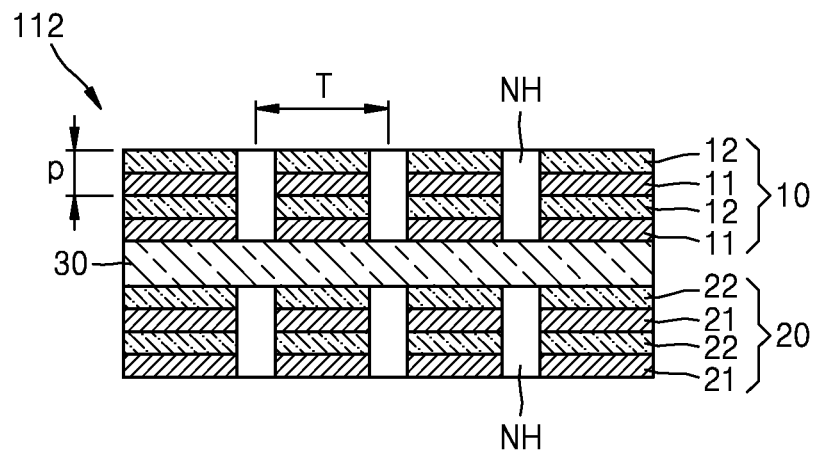
FIG. 5 is a cross-sectional view of a nano antenna cut along a line A-A' in FIG. 4.

FIG. 4 illustrates another exemplary structure of the nano antenna 112 adoptable in the spectro-sensor illustrated in FIG. 1. FIG. 5 is a cross-sectional view of the nano antenna of FIG. 4, taken along a line A-A' as shown in FIG. 4.

The nano antenna 112 may be structured by applying, to a stacked structure of a plurality of dielectric layers, a nano structure which is arranged according to a predetermined rule in a horizontal direction, that is, along a plane which is perpendicular to the stacking direction. Such a structure of the nano antenna 112 may induce a resonance of light in a particular wavelength band along the stacking direction and reduce a resonance wavelength dependency with respect to an incident angle of incident light by a nano structure in the horizontal direction.

More specifically, the nano antenna 112 may include an upper nano-structure layer 10, a lower nano-structure layer 20, and an intermediate layer 30 disposed between the upper nano-structure layer 10 and the lower nano-structure layer 20.

The upper nano-structure layer 10 has a stacked structure in which a first dielectric layer 11 which has a first refractive index and a second dielectric layer 12 which has a second refractive index which is higher than the first refractive index are stacked alternately, and a plurality of nano holes NH formed to pass through the stacked structure.

Like the structure of the upper nano-structure layer 10, the lower nano-structure layer 20 may also have a stacked structure in which a third dielectric layer 21 which has a third refractive index and a fourth dielectric layer 22 which has a fourth refractive index which is higher than the third refractive index are stacked alternately, and a plurality of nano holes NH formed to pass through the stacked structure.

A period p in which different types of dielectric layers are stacked in the upper nano-structure layer 10 and the lower nano-structure layer 20 may be smaller than $\lambda/2$, where $\lambda$ represents a resonance wavelength of the nano antenna 112.

The upper nano-structure layer 10 and the lower nano-structure layer 20 may include a distributed Bragg reflector (DBR), respectively. A thickness of a dielectric layer of the upper nano-structure layer 10 and the lower nano-structure layer 20 may be determined to be equal to ¼ of a resonance wavelength, and materials of a first dielectric layer 11, a second dielectric layer 12, a third dielectric layer 21, and a fourth dielectric layer 22 and the number of pairs of a dielectric layer may be properly adjusted based on a reflectivity. In particular, the number of pairs of the first dielectric layer 11 and the second dielectric layer 12 in the upper nano-structure layer 10 and the number of pairs of the third dielectric layer 21 and the fourth dielectric layer 22 in the lower nano-structure layer 20 are illustrated as being equal to two, but these numbers are only an example, and other numbers therefor may be used.

The reflectivity of the upper nano-structure layer 10 may be the same as or different from that of the lower nano-structure layer 20. For example, the reflectivity of the lower nano-structure layer 20 arranged to be adjacent to the optical detector (121 of FIG. 1) may be set to be lower than the reflectivity of the upper nano-structure layer 10.

The upper nano-structure layer 10 and the lower nano-structure layer 20 may be formed of the same material. In this aspect, the first dielectric layer 11 and the third dielectric layer 21 may be formed of the same material, and the second dielectric layer 12 and the fourth dielectric layer 22 may be formed of the same material. In this case, the reflectivity may be adjusted by making the number of pairs of dielectric layers applied to the upper nano-structure layer 10 and the number of pairs of dielectric layers applied to the lower nano-structure layer 20 different from each other.

The intermediate layer 30 breaks rules of the upper nano-structure layer 10 and the lower nano-structure layer 20 in the nano antenna 112, and a material of the intermediate layer 30 is not specially limited. For example, if the upper nano-structure layer 10 and the lower nano-structure layer 20 are formed of the same material, the intermediate layer 30 may be formed of a material that is different from that of the upper nano-structure layer 10 and the lower nano-structure layer 20, and a thickness of the intermediate layer 30 may vary relatively widely. The same material as that of any one of the dielectric layers of the upper nano-structure layer 10 and the lower nano-structure layer 20 may be used in the intermediate layer 30, and in this case, the intermediate layer 30 may have a different thickness than the dielectric layers used in the upper nano-structure layer 10 and the lower nano-structure layer 20.

A plurality of nano holes NH may be arranged according to a predetermined rule along a plane which is perpendicular to the stacking direction. The period T which corresponds to the rule may be smaller than $\lambda/3$, where $\lambda$ represents the resonance wavelength of the nano antenna 112.

The plurality of nano holes NH may be filled with air or a dielectric material which has a refractive index greater than one. The refractive index of the dielectric material filling the nano hole NH is not limited, and for example, may be equal to or different from the refractive index of any one of the first layer 11, the second dielectric layer 12, the third dielectric layer 21, and the fourth dielectric layer 22.

Figure 6A:
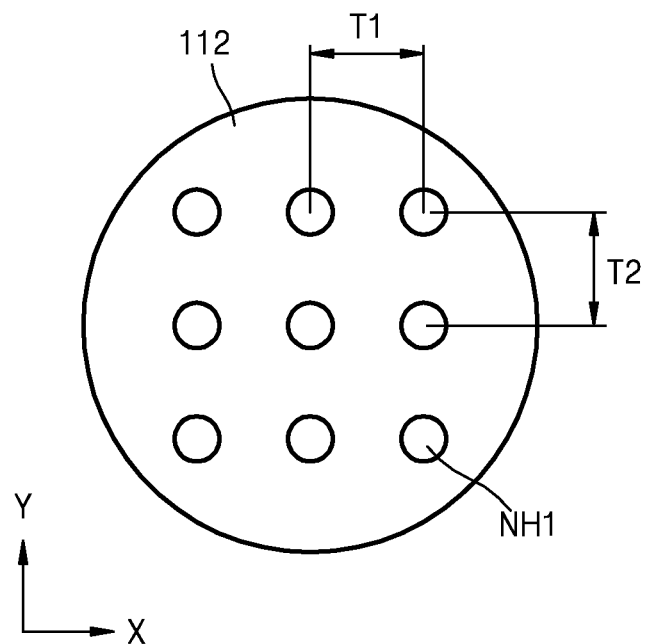
FIGS. 6A, 6B, and 6C illustrate examples of shapes and arrangements of nano holes adoptable in a nano antenna illustrated in FIG. 4.
Figure 6B:
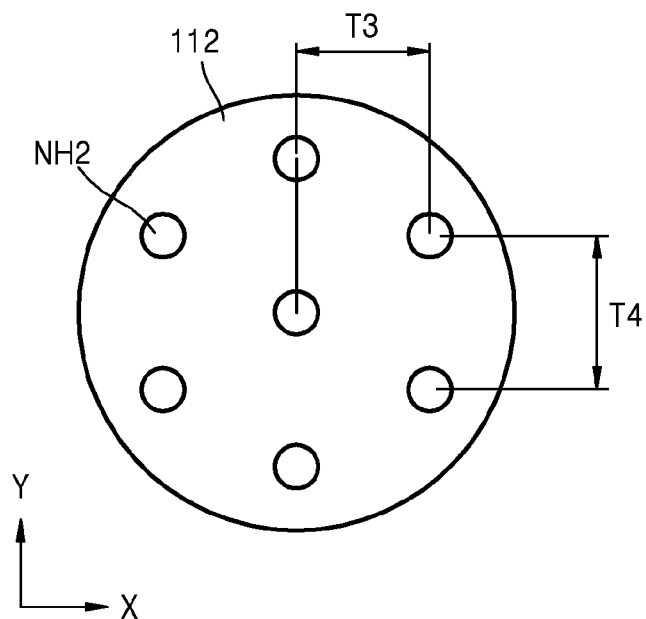

FIGS. 6A and 6B illustrate examples of shapes and arrangements of nano holes adoptable in the nano antenna illustrated in FIG. 4.

Referring to FIG. 6A, a plurality of nano holes NH1 may be arranged in accordance with a period T1 in a first direction and in accordance with a period T2 in a second direction. T1 and T2 may be equal to each other.

Referring to FIG. 6B, a plurality of nano holes NH2 may be repetitively arranged in accordance with a period T4 along a column and repetitively arranged in accordance with a period T3 in a lateral direction, and nano holes NH2 in adjacent columns may arranged alternately. T3 and T4 may be equal to each other.

In FIGS. 6A and 6B, the cross-sectional shape of the nano holes NH1 and NH2 and the nano antennas 112 are illustrated in a circular shape, but this shape is merely an example and is not limited thereto. For example, the cross-sectional shape may be any of an oval shape, a polygonal shape, or the like.

Figure 6C:
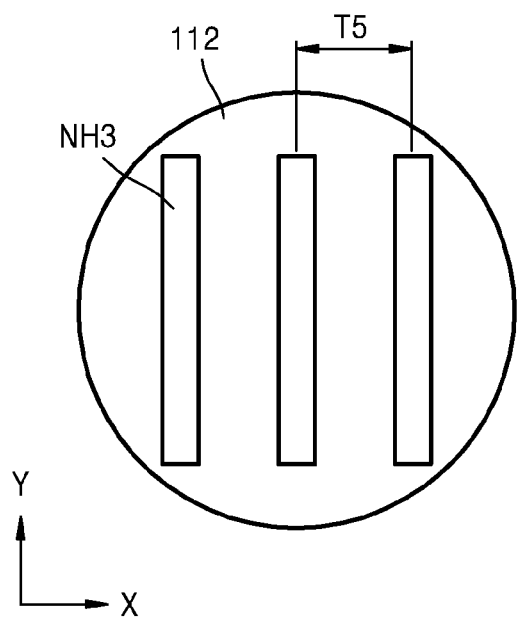

Referring to FIG. 6C, a plurality of nano holes NH3 may be repetitively arranged in accordance with a period T5 in a lateral direction, and the cross-sectional shape of the nano holes NH3 is an elongated rectangular shape.

Figure 7:
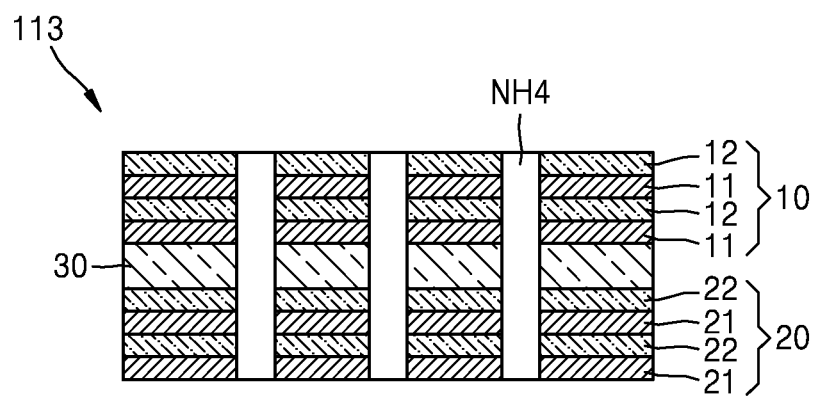
FIG. 7 illustrates another exemplary structure of a nano antenna adoptable in a spectro-sensor illustrated in FIG. 1.

FIG. 7 illustrates further another exemplary structure of the nano antenna adoptable in the spectro-sensor illustrated in FIG. 1.

The nano antenna 113 is different from the nano antenna 112 illustrated in FIG. 4, in that in the nano antenna 113, nano holes NH4 passing through a stacked structure are formed to comprehensively pass through all three layers, including the upper nano-structure layer 10, the intermediate layer 30, and the lower nano-structure layer 20. In particular, the nano holes NH4 formed in the upper nano-structure layer 10 and the nano holes NH4 formed in the lower nano-structure layer 20 are connected to each other by passing through the intermediate layer 30. The shape or arrangement of the nano holes NH4 may have a shape as illustrated in FIGS. 6A and 6B.

When the nano antennas 112 and 113 are adopted in the spectro-sensor 100 in the form of an array as illustrated in FIG. 1, the respective nano antennas 112 and 113 deliver a partial specific wavelength of an optical signal L from a spectroscopic-analysis target to the lower optical detector 121. A material and a thickness of each dielectric stacked structure and details of nano holes may be determined such that the nano antennas 112 and 113 may resonate only specific wavelength components from lights incident at various angles and deliver the wavelength components to the optical detector 121.

Figure 8:
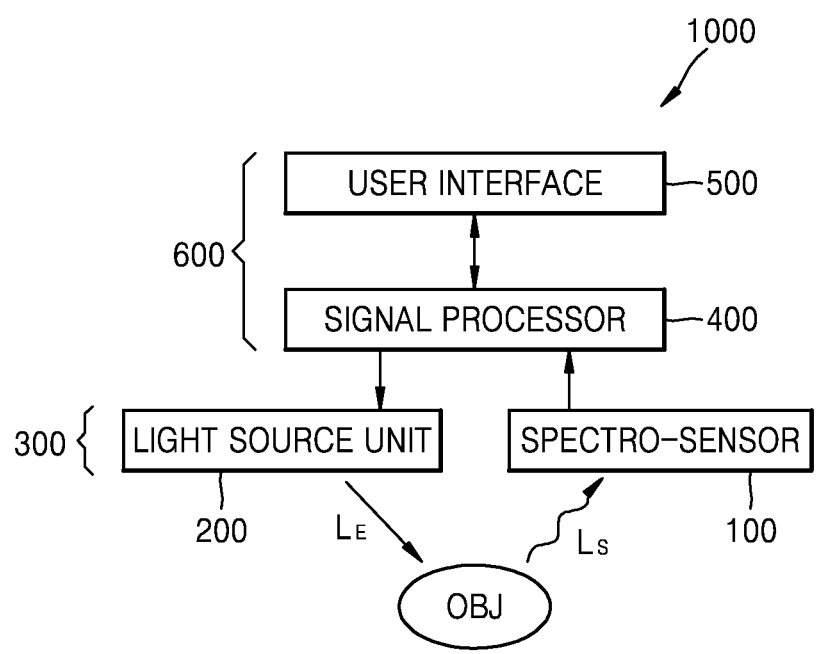
FIG. 8 is a block diagram illustrating a schematic structure of a spectrometer, according to an exemplary embodiment.

FIG. 8 is a block diagram illustrating a schematic structure of a spectrometer, according to an exemplary embodiment.

The spectrometer 1000 includes a spectro-sensor module 300 that irradiates excitation light $L_E$ toward an object OBJ and senses scattered light $L_S$ from the object OBJ. The spectro-sensor module 300 includes a light source unit 200 and a spectro-sensor 100.

Herein, the object OBJ may be any of a living body such as a human body or an animal, food, and/or the like. For example, the object OBJ may be a human body on which a blood sugar level measurement is performed, food on which a freshness measurement is performed, or a sample for analyzing air pollution or water pollution.

The light source unit 200 may include a light source or an optical member configured for directing light from the light source toward a necessary position of the object OBJ. The light source may be structured to irradiate light in a wavelength band which is suitable for a property of the object OBJ to be analyzed. For example, the light source may irradiate light in a near infrared band.

The spectro-sensor 100 may include a nano antenna array and an optical detector array as illustrated in FIG. 1, or may employ any of various forms of nano antennas as illustrated in FIGS. 2A, 2B, 3A through 3E, 4, 5, 6A, 6B, 6C, and 7. The resonance wavelength bands of the nano antennas of the nano antenna array may be set slightly longer than a wavelength of light irradiated from the light source.

The spectrometer 1000 may include a control module 600 that is configured to analyze one or more physical properties of the object OBJ from a signal sensed by the spectro-sensor 100 and to generate a necessary control signal. The control module 600 may include a user interface 500 and a signal processor 400. The user interface 500 may include an input unit and a display unit. The signal processor 400 analyzes the one or more physical properties of the object OBJ based on a signal sensed by the spectro-sensor 100, and may analyze the one or more physical properties of the object OBJ by using, for example, Raman spectroscopy. Raman spectroscopy uses scattering in which light incident to the object OBJ is scattered in various directions after colliding with atoms or molecules of the object OBJ, especially, inelastic scattering. In the scattering, light is absorbed in the atoms or molecules and then emitted, rather than being merely reflected from the surface of the atom or molecule. The scattered light has a wavelength longer than a wavelength of the incident light. Such a wavelength difference may be less than about 200 nm. By analyzing the spectrum of the scattered light, various physical properties, such as vibrations or structure of molecules in the object OBJ, may be recognized.

The signal processor 400 processes the analyzed result into an image signal to be displayed on a display unit of the user interface 500. The signal processor 400 may also output a control signal to the light source unit 200, according to an input received via the user interface 500. If the spectro-sensor 100 is configured such that a resonance wavelength band varies according to an external signal, the signal processor 400 may also generate a control signal for controlling such a variation according to an input which is received via the user interface 500. The signal processor 400 may include a microprocessor or the like.

The spectro-sensor module 300 and the control module 600 may be connected with each other in a wired or wireless manner. For example, the spectrometer 1000 may be implemented with a small-size portable device in which the spectro-sensor module 300 and the control module 600 are connected in a wired manner. Alternatively, the control module 600 may be mounted on a portable mobile communication device and configured to wirelessly communicate with the spectro-sensor module 300.

Figure 9:
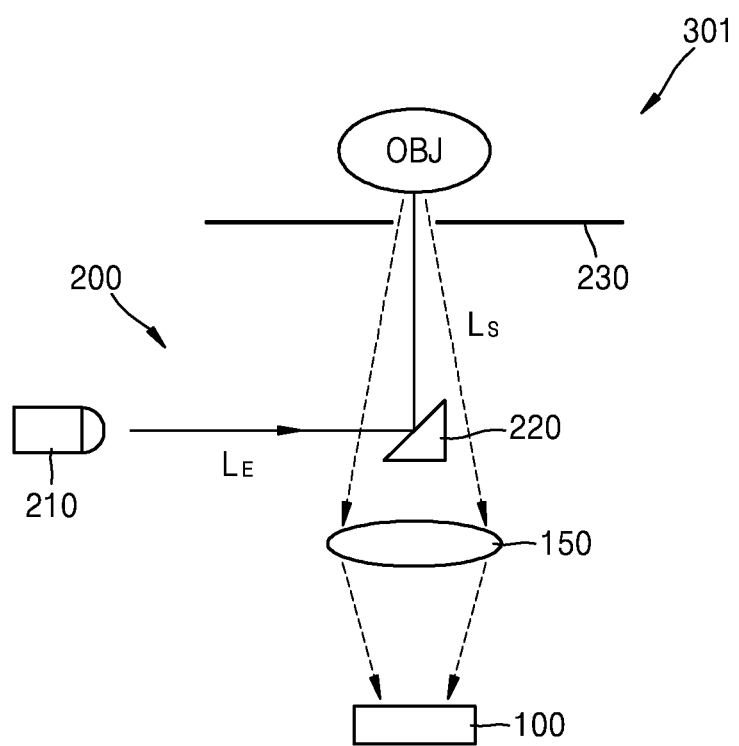
FIG. 9 illustrates an example of optical arrangement of a spectro-sensor module that can be employed in a spectrometer illustrated in FIG. 8.

FIG. 9 illustrates an example of optical arrangement of a spectro-sensor module that can be employed in the spectrometer illustrated in FIG. 8.

The spectro-sensor module 301 may include a light source 210 and the spectrometer 100 and may be of a reflective type. In this aspect, an optical system is configured such that the spectrometer 100 senses the scattered light LS reflected from the object OBJ.

The light source unit 200 may include the light source 210, an optical path change member 220, and an iris 230. The optical path change member 220 is illustrated in the form of a prism, but such an illustration is exemplary, and the optical path change member 220 may be in an alternative form, such as, for example, the form of a beam splitter or a flat panel mirror. The optical path change member 220 may also be omitted according to an arrangement position of the light source 210.

The spectro-sensor module 300 may further include an optical lens 150 that collects the scattered light LS from the object OBJ and causes the collected light to propagate to the spectro-sensor 100.

The excitation light $L_E$ irradiated from the light source 210 collides with a molecular structure in the object OBJ and is absorbed in the molecular structure and then emitted again, and thus, is output from the object OBJ in the form of the wavelength-changed scattered light $L_S$. The scattered light $L_S$ includes various spectrums whose wavelengths vary to different degrees based on a molecular state in the object OBJ. The spectro-sensor module 301 according to the current exemplary embodiment employs an optical system structure in which the scattered light $L_S$ propagating out along the same path as the path along which the excitation light $L_E$ is incident to the object OBJ is incident to the spectro-sensor 100, and if necessary, may further employ an additional optical member that splits and/or redirects the scattered light $L_S$ toward the spectro-sensor 100.

Figure 10:
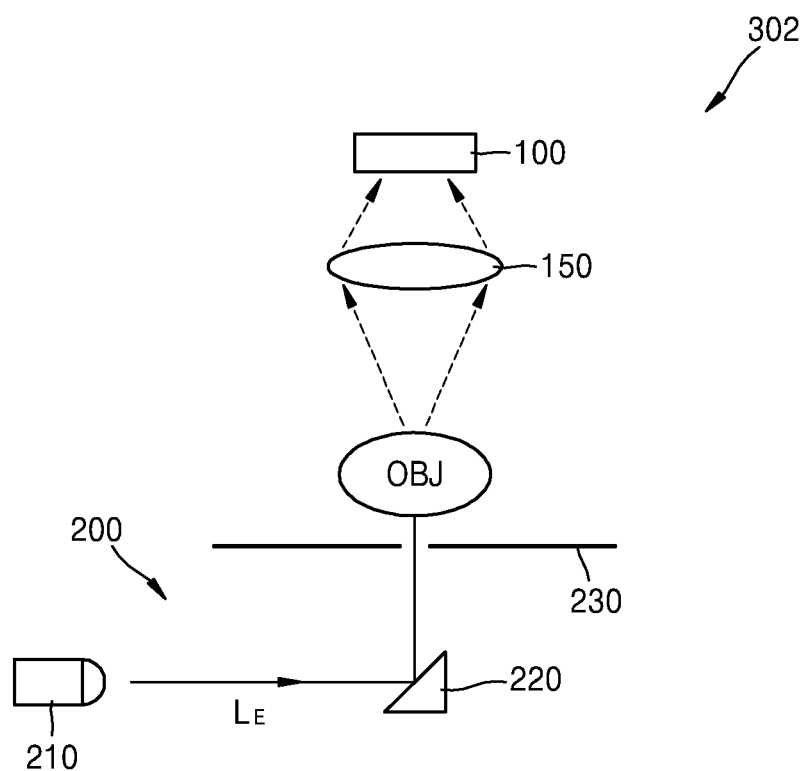
FIG. 10 illustrates another example of optical arrangement of a spectro-sensor module that can be employed in a spectrometer illustrated in FIG. 8.

FIG. 10 illustrates another example of optical arrangement of a spectro-sensor module 302 that can be employed in the spectrometer 1000 of FIG. 8.

The spectro-sensor module 302 may include the light source 210 and the spectrometer 100, and may be of a transmissive type. In particular, the optical system is configured such that the spectro-sensor 100 senses the scattered light $L_S$ which passes through the object OBJ.

The light source unit 200 may include the light source 210, the optical path change member 220, and the iris 230. The optical path change member 220 is illustrated in the form of a prism, but such an illustration is an exemplary one, and the optical path change member 220 may be in an alternative form, such as, for example, the form of a beam splitter or a flat panel mirror. The optical path change member 220 may also be omitted according to an arrangement position of the light source 210.

The spectro-sensor module 302 may further include the optical lens 150 that collects the scattered light $L_S$ from the object OBJ and causes the collected light to propagate to the spectro-sensor 100.

The excitation light $L_E$ irradiated from the light source 210 collides with a molecular structure in the object OBJ and is absorbed in the molecular structure and then emitted again, thus being output from the object OBJ in the form of the wavelength-changed scattered light $L_S$. The scattered light $L_S$ includes various spectrums whose wavelengths vary to different degrees based on a molecular state in the object OBJ. The spectro-sensor module 302 according to the current exemplary embodiment employs an optical system structure in which the scattered light $L_S$ passing through the object OBJ is incident to the spectro-sensor 100.

Whether to employ the reflective type as illustrated in FIG. 9 or the transmissive type as illustrated in FIG. 10 may be properly determined based on the properties of the object OBJ.

Figure 11:
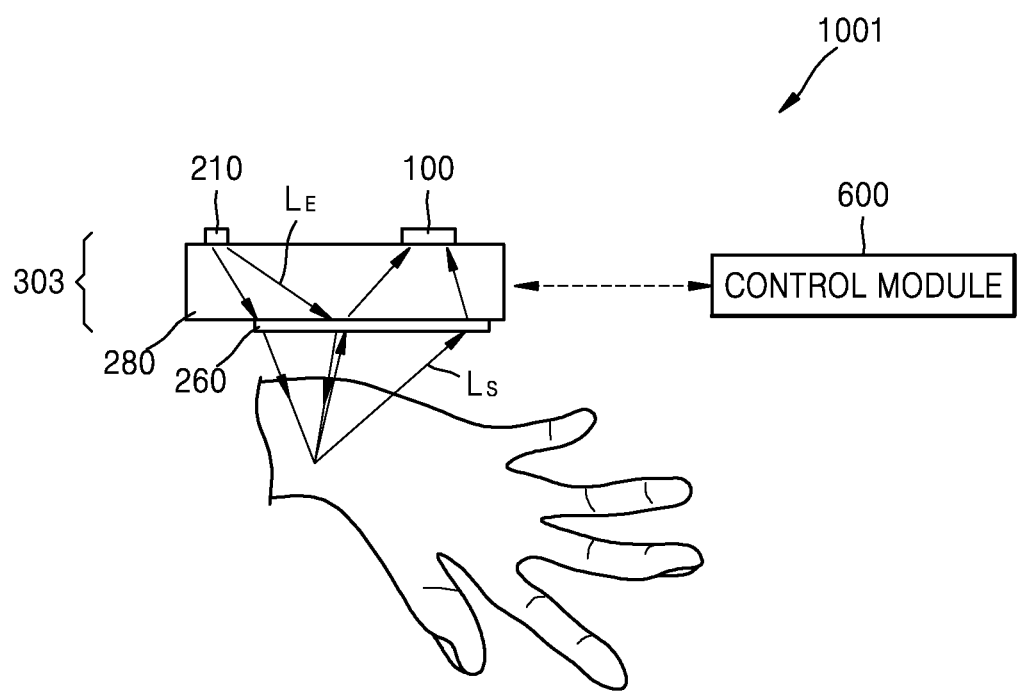
FIG. 11 illustrates a schematic structure of a spectrometer, according to another exemplary embodiment.

FIG. 11 illustrates a schematic structure of a spectrometer, according to another exemplary embodiment.

The spectrometer 1001 may include a spectro-sensor module 303 and the control module 600. In the current exemplary embodiment, the spectro-sensor module 303 may include a base 280 which is made of a transmissive material, and the light source 210 and the spectro-sensor 100 are arranged to be spaced apart from each other on a surface of the base 280.

The light source 210 is arranged to irradiate the excitation light $L_E$ toward the object OBJ through the base 280, and the spectro-sensor 100 is arranged to sense the scattered light $L_S$ incident from the object OBJ through the base 280.

The spectro-sensor module 303 may further include an optical lens 260 that collects the excitation light $L_E$ from the light source 210 and causes the collected excitation light to propagate to the object OBJ, and also collects the scattered light $L_S$ from the object OBJ and causes the collected scattered light to propagate to the spectro-sensor 100. The optical lens 260 may be arranged on a surface which faces a surface of the base 280 on which the light source 210 and the spectro-sensor 100 are arranged.

The base 280 may be made of a flexible material. In this case, the spectro-sensor module 303 is wearable on the object OBJ.

The control module 600 may be connected with the spectro-sensor module 303 in a wired or wireless manner. The control module 600 may be mounted on the base 280 together with the spectro-sensor module 303, and may form, for example, a small-size wearable spectrometer in the form of a bracelet.

Alternatively, the spectrometer may be implemented such that spectro-sensor module 303 is formed as a wearable device in the form of a bracelet and a control module is mounted on a mobile device.

Figure 12:
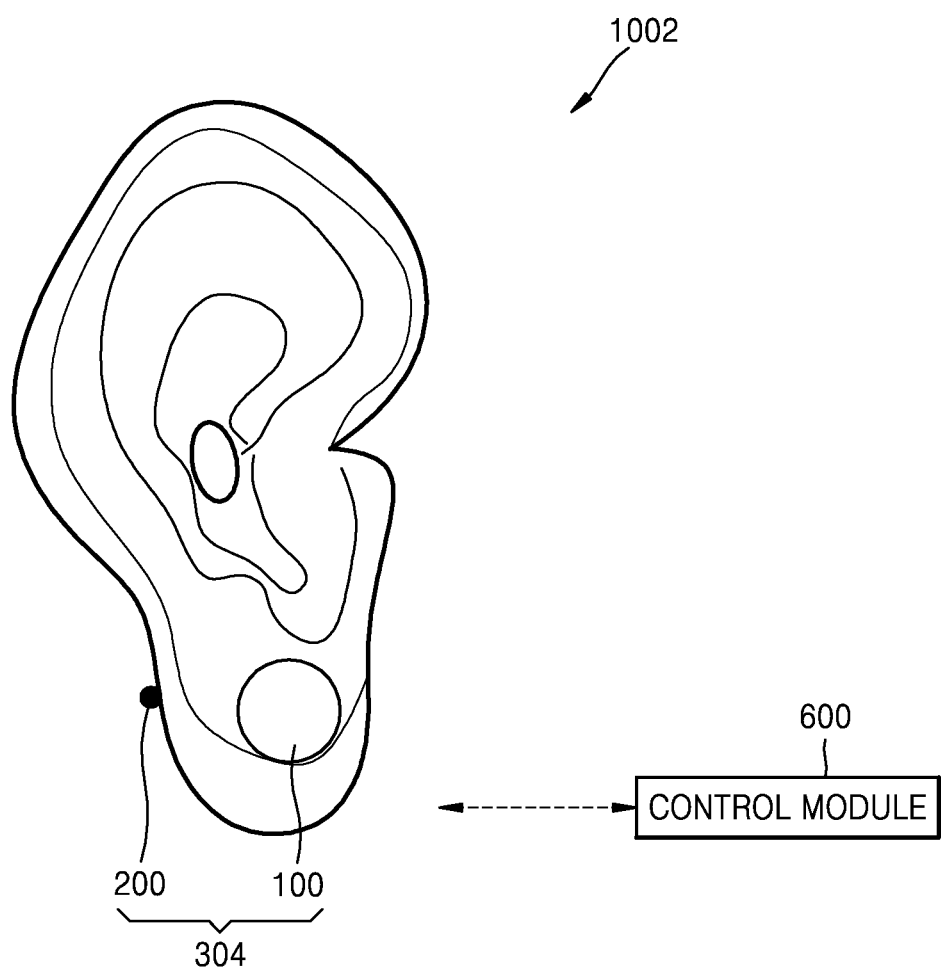
FIG. 12 illustrates a schematic structure of a spectrometer, according to another exemplary embodiment.

FIG. 12 illustrates a schematic structure of a spectrometer, according to another exemplary embodiment.

A spectro-sensor module 304 may include the light source unit 200 and the spectro-sensor 100, and may employ a transmissive optical system to be worn on the object OBJ in the form of an earring.

The control module 600 may be connected with the spectro-sensor module 304 in a wired or wireless manner. For example, the control module 600 may be mounted on a mobile device and may communicate with the spectro-sensor module 304.

The above-described spectro-sensor has a structure in which a nano antenna array and an optical detector array are coupled, and the structure is configured to detect a signal from an object by intensively collecting light on a wavelength basis. Thus, the above-described spectro-sensor has high resolution and high SNR, and may be implemented to have a relatively thin thickness of between approximately several tens of nanometers and several hundreds of nanometers. Therefore, the spectro-sensor is suitable for being applied in the form of a wearable and portable, small-size spectroscope.

Moreover, the above-described spectro-sensor may be manufactured through a relatively simple process because a nano-antenna array forming process may be performed continuously in a semiconductor processing operation for forming an optical detector array.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments has been described with reference to the figures, it will be understood by those of ordinary skill in the art that various changes in form and details may be made therein without departing from the spirit and scope of the present inventive concept as defined by the following claims.

What is claimed is:

1. A spectro-sensor comprising:
a nano antenna array comprising a first nano antenna and at least a second nano antenna that have different respective resonance wavelength bands; and
an optical detector array comprising a first optical detector and at least a second optical detector that respectively detect light from the first nano antenna and the second nano antenna,
wherein each of the first nano antenna and the at least the second nano antenna comprises:
a respective upper nano-structure layer that has a first stacked structure in which a first dielectric layer that has a first refractive index and a second dielectric layer that has a second refractive index that is higher than the first refractive index are alternately stacked along a first direction, and a respective first plurality of nano holes formed to pass through the first stacked structure;
a respective lower nano-structure layer which has a second stacked structure in which a third dielectric layer that has a third refractive index and a fourth dielectric layer that has a fourth refractive index that is higher than the third refractive index are alternately stacked along the first direction, and a respective second plurality of nano holes formed to pass through the second stacked structure; and
a respective intermediate layer of dielectric material disposed between the corresponding upper nano-structure layer and the corresponding lower nano-structure layer.

2. The spectro-sensor of claim 1, wherein the external signal includes at least one from among an electric signal, a sound wave, heat, and a mechanical force.

3. The spectro-sensor of claim 1, wherein a period of the first nano antenna and the at least the second nano antenna that corresponds to the first stacked structure and the second stacked structure is smaller than $\lambda/2$, wherein $\lambda$ represents a resonance wavelength of the first nano antenna and the second nano antenna.

4. The spectro-sensor of claim 1, wherein each of the first plurality of nano holes and the second plurality of nano holes is arranged according to a predetermined rule on a plane perpendicular to the first direction.

5. The spectro-sensor of claim 4, wherein a period that corresponds to the predetermined rule is smaller than $\lambda/3$, wherein $\lambda$ represents a resonance wavelength of the first nano antenna and the at least the second nano antenna.

6. The spectro-sensor of claim 1, wherein the first dielectric layer and the third dielectric layer are formed of a first same material, and the second dielectric layer and the fourth dielectric layer are formed of a second same material.

7. The spectro-sensor of claim 1, wherein each of the plurality of nano holes is filled with at least one from among air and a dielectric material which has a refractive index greater than one.

8. The spectro-sensor of claim 1, wherein each of the plurality of nano holes formed in the upper nano-structure layer is connected to a corresponding one of the plurality of nano holes formed in the lower nano-structure layer by passing through the intermediate layer.

9. A spectro-sensor module comprising:
a light source configured to irradiate excitation light toward an object; and
the spectro-sensor of claim 1, the spectro-sensor configured to sense scattered light incident thereon that originates from the irradiated excitation light.

10. The spectro-sensor module of claim 9, wherein the spectro-sensor is configured to sense the scattered light reflected from the object.

11. The spectro-sensor module of claim 9, wherein the spectro-sensor is configured to sense the scattered light which passes through the object.

12. The spectro-sensor module of claim 11, wherein the spectro-sensor module is configured to be worn on the object in a form of an earring.

13. A spectrometer comprising:
a spectro-sensor module comprising a light source configured to irradiate excitation light toward an object and the spectro-sensor of claim 1, the spectro-sensor configured to sense scattered light incident thereon that originates from the irradiated excitation light; and
a signal processor configured to analyze at least one physical property of the object based on a signal output by the spectro-sensor.

14. The spectrometer of claim 13, wherein the light source is further configured to irradiate light in a near infrared band.

15. The spectrometer of claim 14, wherein the signal processor is further configured to analyze the at least one physical property of the object by using Raman spectroscopy.

16. The spectrometer of claim 13, wherein the spectro-sensor module is configured to be worn on the object.

17. A spectro-sensor module comprising:
a light source configured to irradiate excitation light toward an object; and
a spectro-sensor, the spectro-sensor comprising:
a nano antenna array comprising a first nano antenna and at least a second nano antenna that have different respective resonance wavelength bands, and
an optical detector array comprising a first optical detector and at least a second optical detector that respectively detect light from the first nano antenna and the second nano antenna,
wherein the spectro-sensor is configured to sense the scattered light reflected from the object, and further comprises a base formed of a transmissive material and comprising a first surface and a second surface that faces the first surface,
wherein the light source is arranged on the first surface and configured to irradiate the excitation light toward the object through the second surface, and
wherein the spectro-sensor is arranged on the first surface and configured to sense the scattered light incident from the object through the second surface.

18. The spectro-sensor module of claim 17, further comprising an optical lens arranged on the second surface and configured to collect the excitation light irradiated from the light source toward the object and to collect the scattered light scattered from the object.

19. The spectro-sensor module of claim 17, wherein the transmissive material is flexible.

20. The spectro-sensor module of claim 19, wherein the spectro-sensor module is configured to be worn on the object.

21. A method for performing spectroscopy, comprising:
arranging a plurality of nano antennas which have different respective resonance wavelength bands and which are configured to emit light; and
detecting, by an array of optical detectors, the light emitted from the plurality of nano antennas,
the method further comprising, for each of the plurality of nano antennas:
alternately stacking a first dielectric layer which has a first refractive index and a second dielectric layer which has a second refractive index which is higher than the first refractive index in a first direction in order to form an upper nano-structure layer;
forming a first plurality of nano holes which pass through the upper nano-structure layer;
alternately stacking a third dielectric layer which has a third refractive index and a fourth dielectric layer which has a fourth refractive index which is higher than the third refractive index in the first direction in order to form a lower nano-structure layer;
forming a second plurality of nano holes which pass through the lower nano-structure layer; and
combining the upper nano-structure layer and the lower nano-structure layer with an intermediate layer which comprises a dielectric material and which is disposed between the upper nano-structure layer and the lower nano-structure layer.

22. The method of claim 21, wherein for each of the plurality of nano antennas, a period which corresponds to each of the upper nano-structure layer and the lower nano-structure layer is smaller than $\lambda/2$ in which $\lambda$ represents a resonance wavelength of the corresponding nano antenna.

23. The method of claim 21, wherein each of the first plurality of nano holes and the second plurality of nano holes is arranged on a plane that is perpendicular to the first direction.

* * * * *